Nov. 19, 1974 R. S. MOORE Plant Pat. 3,654
MINIATURE ROSE PLANT
Filed Dec. 26, 1973
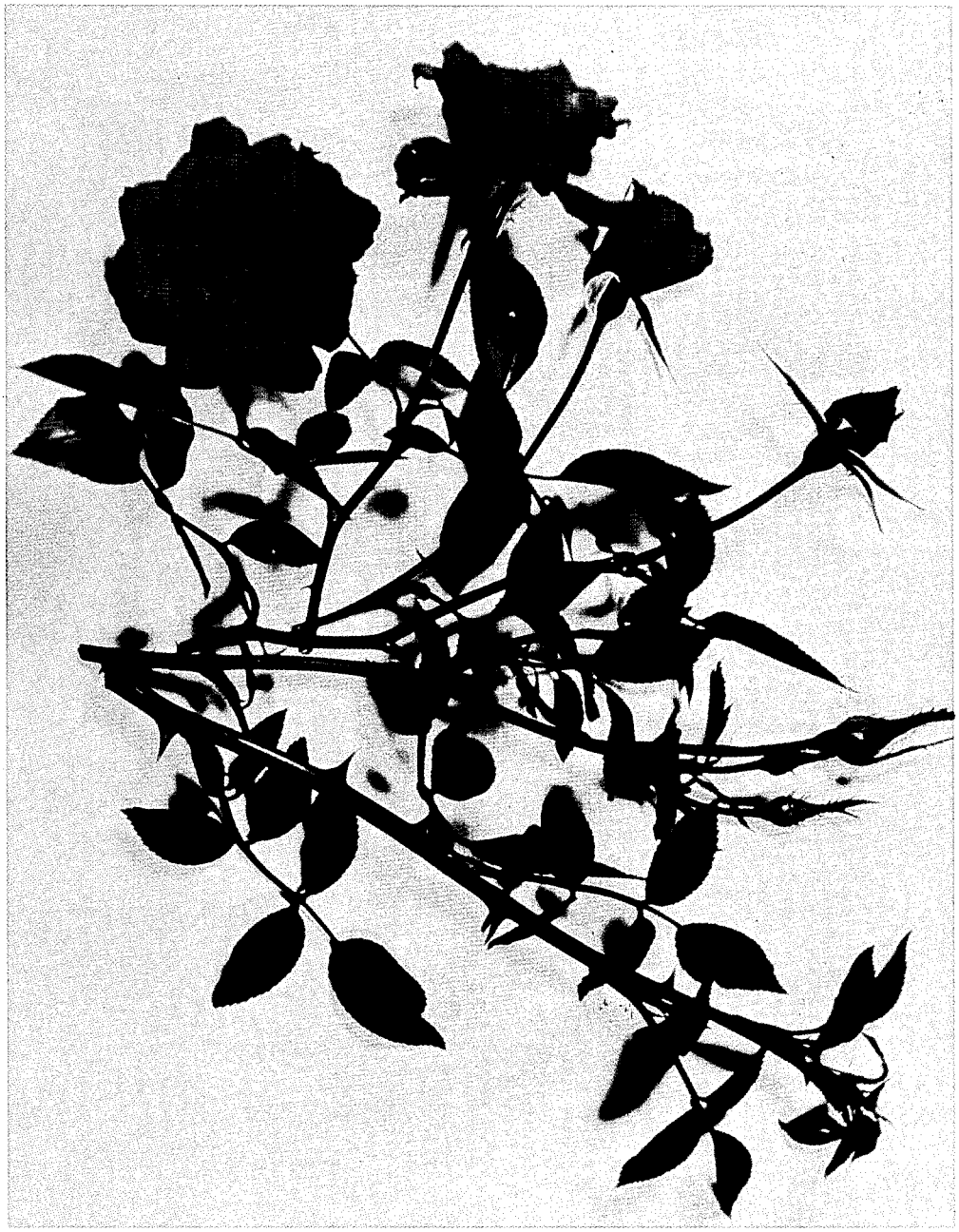

United States Patent Office

Plant Pat. 3,654
Patented Nov. 19, 1974

3,654

MINIATURE ROSE PLANT

Ralph S. Moore, 2519 E. Noble Ave.,
Visalia, Calif. 93277

Filed Dec. 26, 1973, Ser. No. 428,310
Int. Cl. A01h *5/00*
U.S. Cl. Plt.—10 1 Claim

ABSTRACT OF THE DISCLOSURE

The present invention relates to a new and distinct variety of hardy, dwarf, bush type rose plant of the miniature class; the variety being primarily characterized—as to novelty—by dark red buds and flowers which in general color effect are a very dark red similar in color to "Dwarf King" (Miniature—Patent No. 1577, expired) and which tend to become darker red as the flower matures.

The variety is further characterized by:

An abundance of bloom, with flowers borne singly or several to the stem in loose clusters.

Little or no fragrance.

SUMMARY OF THE INVENTION

A plant which is vigorous, of rounded upright shape and with flat to semi-glossy, moderately small foliage with pointed leaflets; the buds and flowers being similar in form to "Baccara" (Plant Patent No. 1,367, expired) but much smaller in size. The plant, which has a normal height of 10 to 14 inches, can easily be maintained at a lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, California, under conditions of careful control and observation, as a cross between "Baccara" (H.T.—Plant Patent No. 1,367, expired) as the seed parent and "Magic Wand" (Miniature—not patented) as the pollen parent.

Subsequent to origination of the variety I successfully asexually reproduced it, in my nursery located as aforesaid, by budding as well as by cuttings, the reproductions having run true in all respects.

BRIEF DESCRIPTION OF DRAWING

The color photo illustrates a spray, including foliage, buds and flowers.

Referring now specifically to the new and distinct variety of miniature rose plant, the following is a detailed description thereof in outline; all major plate identifications being by reference to the British Colour Council Horticultural Colour Chart, except where common terms of color definition are employed.

Type: Hardy; dwarf; bush; seedling; greenhouse; outdoors; cut flowers, garden decoration; potted plant.

Class: Miniature.

Flowers: Continuity; continuous—repeat bloom all season. Fragrance; little or none.

Flowers borne: Usually singly but may come several together (3–5) on strong, medium length stems.

Quantity of bloom: Abundant both outside and in greenhouse.

Bud:

*Peduncle.*—Extra long; slender but sturdy; erect; medium green, often tinted bronze; hairs—few to none. Before calyx breaks; size—small. Form—medium long; pointed; few foliaceous appendages and few or no tiny short hairs on surface of bud; with foliaceous parts extending beyond the tip of the bud equal to one half or more of its length.

*Color.*—Medium green, often tinted with bronze. As calyx breaks, color—deep to blackish red. As first petal opens: substantially same color; size—small.

Bloom: Size when fully open—small averaging about 1¼" to 1½". Petalage—double, 35–40 (plus several narrow petaloids) arranged reguluarly. Form—full, high centered at first, becoming more rounded, with petals rolled loosely outward, and later at maturity rounded with higher center with petals rolled loosely outward and downward. Edges of petals tend to fold upward imparting a slightly quilled or pointed effect.

*Petals.*—Fairly thick; satiny both inside and outside.

*Shape.*—Outside petals, broad lanceolate (almost round with pointed base); intermediate; broad lanceolate with rounded tips; inside—lanceolate with acute tip.

*Color.*—Newly opened flower from a plant grown outdoors (October 1973), Visalia, California.

*Outside petal.*—Outside surface — Chrysanthemum Crimson—824 (often with darker shading) sometimes near Ruby Red 827; inside surface—Chrysanthemum Crimson 824 (sometimes with some darker and/or lighter shading) and a very small area of near white at base.

*Intermediate petal.*—Outside surface—same as outside petal, inside surface—same as outside petal.

*Inner petal.*—Outside surface—same as intermediate petal; inside surface—same as intermediate petal. General color effect newly opened flowers—deep red color, similar to "Dwarf King" but with a fluorescent glow or undertone similar to that of "Baccara" (seed parent).

*Three days open.*—Darker red color.

*Behavior.*—As flowers age petals may become darker shade before dropping off. Spent petals drop off. Flower color is often lighter red shade when grown in greenhouse.

*Flower longevity* (October 1973).—Bush in garden or pot 7–10 days or longer. Cut flowers at living room temperature, 6 days or longer.

Reproductive Organs:

*Stamens.*—Few to average, arranged regularly about pistil; sometimes mixed with petaloids.

*Filaments.*—Short; yellow.

*Pollen.*—None.

*Pistils.*—Average number.

*Styles.*—Uneven; short; bunched; color—orange to

*Stigma.*—Nearly white or pale yellow.

*Ovaries.*—All enclosed in calyx.

*Hips.*—None.

*Sepals.*—Permanent; spear shaped; recurved.

*Seeds.*—None.

Foliage:

Leaves: compound of five leaflets, sometimes seven; average abundance; moderately small; leathery, flat (dull) to semi-glossy.

Leaflets:

*Shape.*—Lanceolate; apex acute; base acute or rounded. Margin serrate.

*Color.*—Normal green; new growth—reddish or tinted bronze (often quite dark).

*Rachis.*—Medium strength; upper side few small hairs or prickles, grooved; underside sparsely thorny with few very tiny prickles.

*Stipules.*—Fairly long; medium width; medium length narrow points which may turn out at both more or less than 45 degrees.

Growth:

*Habit.*—Dwarf; bushy; rounded; much branched.

Growth: free; vigorous.

Canes: medium; slender.

Main stems: color—dull green, sometimes reddish or bronze. Thorns—average; medium length; hooked slightly downward; color—brown or reddish-brown. Prickles—none. Hairs—none.

Branches: color—medium green, sometimes reddish or bronze. Thorns—moderately thorny. Medium length; slender; nearly straight; medium to short oval base. Prickles—none. Hairs—none.

New Shoots: color—usually tinted red or bronze. Thorns—few to moderate; medium length; nearly straight, reddish color; sharp points; base oval. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

1. A new and distinct variety (cultivar) of miniature rose plant of hardy, dwarf, rounded, much branched bush type, as illustrated and described, characterized by buds and flowers resembling the "Baccara" (Plant Patent 1,367, expired) hybrid tea rose in general form (only in miniature), the color being a darker shade of red and the open flower having a similar fluorescent glow; the general color effect being dark red similar to "Dwarf King," easy to propagate from cuttings; with medium small dull to semi-glossy foliage, tinted reddish on new growth; with flowers of above average lasting quality borne singly or several to stem in loose clusters.

No references cited.

ROBERT E. BAGWILL, Primary Examiner